(12) United States Patent
Comings et al.

(10) Patent No.: US 8,034,794 B2
(45) Date of Patent: Oct. 11, 2011

(54) METHODS AND COMPOSITIONS FOR ACID PHOSPHATASE-1 GENE INHIBITION

(76) Inventors: David E. Comings, Duarte, CA (US); James P. MacMurray, Loma Linda, CA (US); Nunzio Bottini, La Jolla, CA (US)

( * ) Notice: Subject to any disclaimer, the term of this patent is extended or adjusted under 35 U.S.C. 154(b) by 0 days.

(21) Appl. No.: 12/835,678

(22) Filed: Jul. 13, 2010

(65) Prior Publication Data

US 2010/0280103 A1 Nov. 4, 2010

Related U.S. Application Data

(60) Division of application No. 12/056,624, filed on Mar. 27, 2008, now abandoned, which is a continuation of application No. 10/493,881, filed as application No. PCT/US02/34500 on Oct. 29, 2002, now abandoned.

(60) Provisional application No. 60/330,693, filed on Oct. 29, 2001.

(51) Int. Cl.
*A61K 48/00* (2006.01)
*C07H 21/04* (2006.01)
*C12Q 1/68* (2006.01)

(52) U.S. Cl. ............... 514/44 A; 536/23.1; 536/24.5; 435/6; 435/325; 435/375

(58) Field of Classification Search .................. None
See application file for complete search history.

*Primary Examiner* — Doug Schultz
(74) *Attorney, Agent, or Firm* — Themis Law

(57) ABSTRACT

The ACP1 *A allele provides a means for diagnosing susceptibility of a human subject to hyperlipidemia, especially hyperlipidemia associated with metabolic syndrome, a means for treating, or preventing the onset of, hyperlipidemia and metabolic syndrome, and a means for screening and identifying drugs suitable for use in treating or preventing hyperlipidemia, especially hyperlipidemia associated with metabolic syndrome. Diagnostic kits are also provided.

4 Claims, 1 Drawing Sheet

METHODS AND COMPOSITIONS FOR ACID PHOSPHATASE-1 GENE INHIBITION

This application is a divisional application of prior co-pending application U.S. Ser. No. 12/056,624 filed Mar. 27, 2008, now abandoned, which is a continuation of application U.S. Ser. No. 10/493,881, filed Sep. 17, 2004, now abandoned, which is a 35 U.S.C. 371 national phase entry application from PCT/US02/34500, filed Oct. 29, 2002, which claims the benefit of U.S. provisional application Ser. No. 60/330,693, filed Oct. 29, 2001. The disclosures of each of the above applications are hereby incorporated herein in their entirety by reference.

FIELD OF THE INVENTION

This invention relates generally to the field of human genetics. More specifically, the invention relates to diagnosis of susceptibility to hyperlipidemia, especially hyperlipidemia associated with metabolic syndrome. The invention further relates to methods for screening drug candidates for suitability in the treatment of hyperlipidemia and metabolic syndrome, and to methods for treating or preventing hyperlipidemia, especially hyperlipidemia associated with metabolic syndrome.

The publications and other materials used herein to illuminate the background of the invention or provide additional details respecting the practice are incorporated by reference.

BACKGROUND OF THE INVENTION

Increased incidence of obesity, hyperlipidemia, hypertension, non-insulin dependent diabetes and coronary artery disease often cluster in the same individuals, and it has been frequently asserted that a common mechanism may be responsible for the comorbidity of these conditions in a subset of the population. The risk factor constellation for this group is often referred to as the "metabolic syndrome", "insulin resistance syndrome" or "syndrome X". The prevalence of the metabolic syndrome is roughly 2.5% in individuals under 40 years of age, rising to 5 to 10% in middle aged and older persons (1). The reasons for this increase in risk is largely due to the corollary age-related increase in obesity, and in particular abdominal obesity in the U.S. population. Obesity is now estimated to be the second leading preventable cause of death after cigarette smoking in the U.S. (2). Thirty-nine million Americans are estimated to be obese (having a body-mass-index (BMI) of ≧30) and an additional 57 million are estimated to be overweight (BMI between 25 and 29). Abdominal obesity, which increases with age among men and postmenopausal women, is responsible for most of the association of obesity with the metabolic syndrome and associated diseases (3). In addition to insulin resistance and hypertension, the principal abnormalities associated with the metabolic syndrome in obese individuals include elevated triglyceride levels and elevated cholesterol/HDL ratio. Increases both in triglyceride and cholesterol/HDL ratio are now recognized as independent risk factors for coronary artery disease (CAD) as well as overall 5-year mortality (4). However, it has remained unclear what distinguishes those individuals whose weight gain leads to the development of the metabolic syndrome from those more fortunate persons who appear capable of considerable weight gain without experiencing the dyslipidemia and insulin resistance that trigger increased risk of developing CAD and non-insulin-dependent diabetes mellitus (NIDDM).

The acid phosphatase locus 1 (ACP1) encodes a low molecular weight protein tyrosine phosphatase (LMPTP) involved in the negative modulation of insulin signal transduction (5). The ACP1 gene product is present ubiquitously in human tissues in two isoforms, called LMPTP-A and -B (6). The same locus also encodes the adipocyte LMPTP, which also is indicated as adipocyte acid phosphatase (HAAP), and is able to dephosphorylate in vitro the tyrosine phosphorylated adipocyte lipid binding protein (ALBP) (7).

ACP1 shows genetic polymorphism corresponding to strong variations in total enzymatic activity and in the ratio between the activity of the two isoforms associated with the different genotypes (8). A positive association between those ACP1 genotypes associated with a low total enzymatic activity and extreme values of BMI in obese children and adult subjects (9, 10, 11) and in non-dyslipidemic NIDDM subjects (12) has been reported in the Italian population. In 11 Italian studies the ACP1 polymorphism has been found to be associated with clinical variability of obesity, but not with the disease itself. The ACP1 *A allele is a variation of the A allele, distinguished by a Gln to Arg substitution at position 105 of the encoded protein, and lower enzymatic activity. In a recent study by Lucarini et al., a highly significant positive association between the ACP1 *A allele (associated with a reduced total enzymatic activity) and BMI has been described, but only in those cases with blood lipid levels (BLL) in the normal range (12).

SUMMARY OF THE INVENTION

The present invention provides diagnostic and prognostic methods for detecting a predisposition to hyperlipidemia, especially hyperlipidemia associated with metabolic disease, by detecting a non-*A allele at the APC1 locus, or confirming the lack of a predisposition by detecting the presence of the *A allele at the APC1 locus. Methods of treating, or reducing the probability of developing hyperlipidemia and metabolic disease are also provided.

In one embodiment, the invention provides a non-human animal which carries a human ACP1 allele in its genome. In another embodiment, the invention provides a cell line derived from one or more cells from a non-human animal.

The invention further provides a method for diagnosing in a human subject a susceptibility to hyperlipidemia, especially hyperlipidemia associated with metabolic syndrome, comprising testing the subject for the presence of a non-*A ACP1 allele, such presence being an indicator of susceptibility to hyperlipidemia.

The invention further provides methods for treating, or preventing the onset of, hyperlipidemia and metabolic disorder in susceptible individuals, comprising inhibiting the activity of the ACP1 enzyme. An alternative method comprises inhibiting the transcription or translation of a non-*A ACP1 gene allele.

The invention further provides a method for identifying a drug product having preventative or curative activity against hyperlipidemia and metabolic syndrome, comprising measuring the activity of an ACP1 enzyme in cells expressing a non-*A allele of the ACP1 gene, to obtain a first enzyme activity value, exposing cells expressing the non-*A allele of the ACP1 enzyme to a drug candidate, measuring ACP1 enzyme activity to obtain a second enzyme activity value, comparing the first enzyme activity value to the second enzyme activity value to obtain an enzyme activity ratio, a ratio of greater than 1 being an indicator of preventative or curative activity against hyperlipidemia, especially hyperlipidemia associated with metabolic syndrome.

The invention further provides diagnostic kits for use in identifying persons who are at risk of developing hyperlipidemia, especially hyperlipidemia associated with metabolic syndrome, comprising a means for screening for the presence or absence of a non-*A allele of the ACP1 gene, and a means for identifying the presence of said non-*A allele, such presence indicating that the person is at risk of developing hyperlipidemia. Screening can be accomplished by providing a means for identifying in a sample the presence of DNA encoding a non-*A ACP1 enzyme. Alternatively, screening can be accomplished by providing a means suitable for measuring the activity of an ACP1 enzyme in a sample, and comparing the activity measurement to the activity of an ACP1 *A standard.

The invention further provides a method of screening for drug candidates useful in treating a disease or condition associated with a non-*A ACP1 allele, wherein the method comprises administering a drug to an animal which is heterozygous or homozygous for the allele, wherein if the animal shows a decrease in signs or symptoms associated with the disease when compared to an animal that is heterozygous or homozygous for that allele and that does not receive the drug, the drug is a drug candidate for treating that disease. In a preferred embodiment, the condition is metabolic syndrome. An alternative method comprises exposing a cell, or culture of cells, comprising a non-*A ACP1 allele to a drug candidate, and subsequently measuring ACP1 activity, a reduction in activity relative to an untreated control indicating suitability of the drug candidate for treatment of hyperlipidemia, especially hyperlipidemia associated with metabolic disorder, or prevention of its onset.

DETAILED DESCRIPTION OF THE INVENTION

Figure 1:
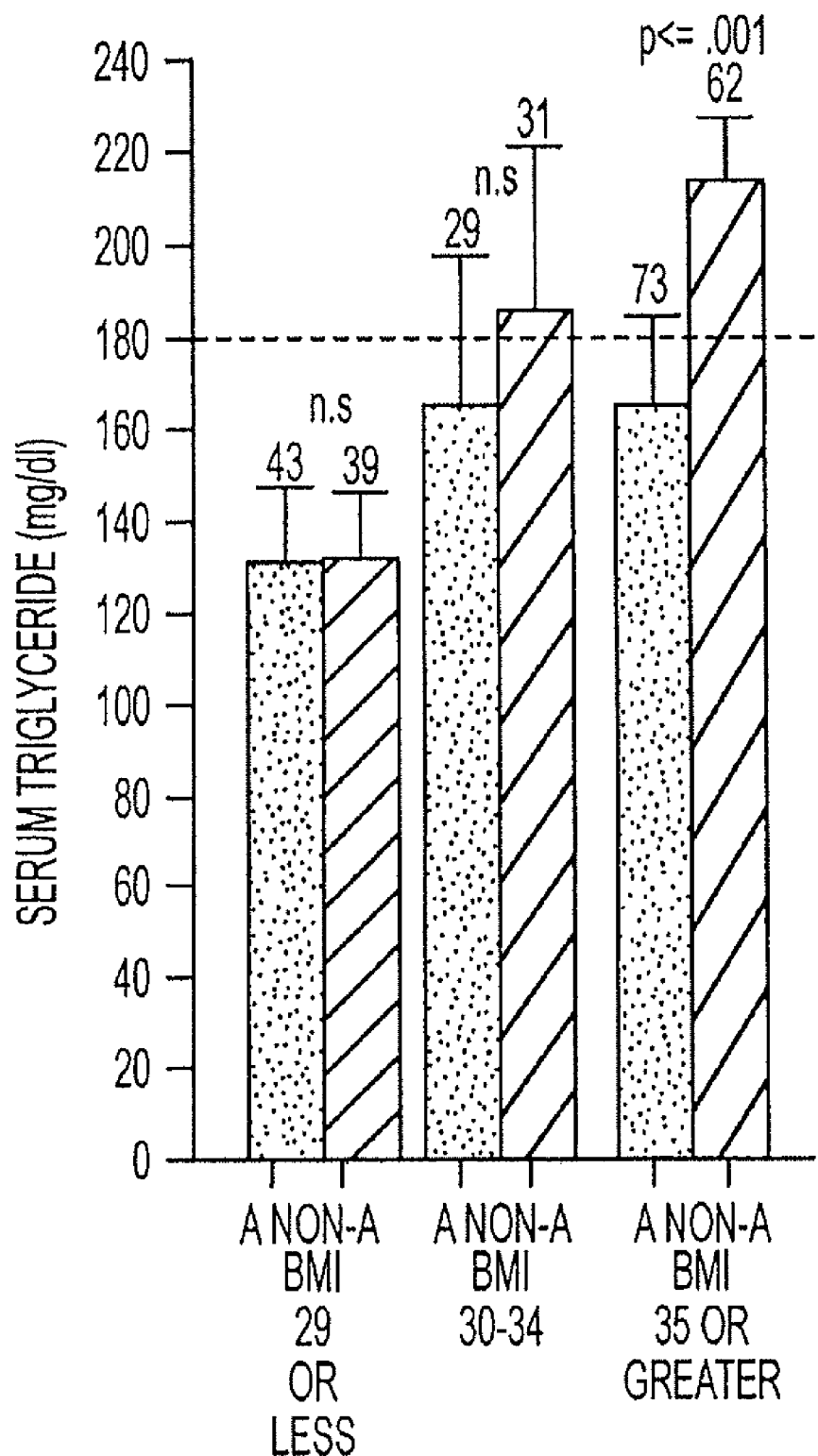
FIG. 1 shows the relationship between ACP1 polymorphism and triglyceride levels for subjects grouped according to their classification as non-obese, obese or morbidly obese.

In an investigation of the relationship between ACP1 polymorphism and metabolic variables in 173 Caucasian American post-menopausal obese subjects and 76 age matched non-obese control subjects, ACP1 genotypes were found to be significantly associated with elevated levels of total cholesterol ($p=0.005$) and triglyceride ($p=0.006$) in obese women only. The association between ACP1 polymorphism and blood lipid levels in obese women was mainly due to an age-independent protective effect of the *A allele against hyperlipidemia. The protective effect on triglycerides was positively correlated with BMI in obese subjects and was marked in morbidly obese subjects. It has been unclear why some individuals who gain weight develop dyslipidemia. and other aspects of the metabolic syndrome, while others do not. The strong protective effect that the ACP1 *A allele exerts against the development of hypertriglyceridemia in obese subjects, indicates that those who gain weight and carry the ACP1 *A allele are the ones who do not develop the metabolic syndrome.

Obese women carrying the *A allele, associated with a reduced total enzymatic activity, show a tendency toward higher degrees of obesity. The weaker association between ACP1 polymorphism and degree of obesity in the present data compared to the Italian samples of an earlier study could be due to differences in the BMI distribution that is very different between the two samples (91% of the present study subjects show a BMI value over 32).

A highly significant association of ACP1 polymorphism with BLL is present in the obese sample and the data indicate that most of the association of ACP1 polymorphism with BLL was at the Taql SNP. This SNP distinguishes the presence or absence of the *A allele, which is associated with low levels of total enzymatic activity and a high ratio between A and B isoform production. The Taql SNP leads also to the incorporation of an Arg instead of a Gln in position 105 of both the LMPTP isoforms in the protein product of the ACP1 *A allele (16).

Interestingly, the effect of the ACP1 gene on triglyceride levels depends on BMI: individuals carrying the ACP1 *A allele are protected from the hypertriglyceridemia that follows the increase of BMI between overweight and obese subjects, suggesting that ACP1 is a gene influencing the predisposition at least to some features of the metabolic syndrome that is associated with central obesity (3). It seems possible that an ACP1 isoform is acting with high specificity on some pathway responsible for the regulation of fatty acid absorption and/or metabolism in obese subjects. The results of correlation analysis with the enzymatic parameters associated with ACP1 genotypes suggest that the LMPTP *A isoform is involved in mediating the association between ACP1 and the clinical variability of obesity. Another possibility that doesn't exclude the latter is that such association is due to the different affinity of the two enzyme variants (Gln105 and Arg105) for specific substrates in the adipocytes and/or in other tissues.

LMPTP is involved in the in vitro negative modulation of insulin signal transduction (17). LMPTP is also able to in vitro dephosphorylate the adipocyte lipid binding protein (ALBP or pp15) (7). ALBP belongs to a family of lipid binding proteins present in various isoforms in many human tissues. In adipose tissue ALBP is phosphorylated on Tyr19 after insulin stimulation and this phenomenon seems to impair its fatty acid binding ability (18). In the adipose tissue the double activity of LMPTP (on insulin receptor signal transduction and ALBP phosphorylation) could partly compensate each other, thus explaining the weaker association between ACP1 genotypes and overall BMI. In fact, LMPTP could at the same time counteract the adipogenic stimulus mediated by the insulin receptor and contribute to ALBP dephosphorylation which causes an increase of its lipid binding activity.

As a result of previous studies, the ACP1 locus is currently included among the candidate "modifier" loci in obesity (19). The association of ACP1 with BLL and/or BMI is present only in obese subjects in all the samples studied to date, and as shown in FIG. 1, the effect of ACP1 on triglycerides is more evident in higher classes of BMI. No linkage study has shown the 2p25 region (the locus of ACP1) to be associated with obesity. Indeed, linkage analysis has less chance of revealing the role of "modifier" genes that are acting only when other genes involved in the disease predisposition are present, i.e. epistasis.

Insulin signal transduction is well known to be modulated by other cytosolic tyrosine phosphatases that act with higher affinity than LMPTP (20). Two transmembrane phosphatases in adipocytes have been isolated that are responsible for dephosphorylating ALBP with high affinity (21). We propose that the effect of LMPTP becomes evident in the regulation of metabolic signaling only in pathological situations, when other control systems usually acting with higher affinity are failing. Recently the tyrosine phosphorylated caveolin has been proposed as a possible physiological substrate of LMPTP (22). Caveolin is expressed at high levels only in very differentiated tissues such as endothelial tissue and adipocytes. In these tissues the reversible phosphorylation of caveolin on tyrosine residues is involved in the modulation of signal transduction through many receptors (23). Following the expansion of adipose tissue in obese subjects the interaction between caveolin and LMPTP could become the limiting factor for one or more signal transduction pathways affecting lipid absorption and/or metabolism that are normally regulated mainly through other mechanisms.

In summary, the presence of the ACP1 *A allele exerts an independent protective effect against the hypertriglyceridemia associated with increases in BMI into the obese range. Because most of the lethality and morbidity connected with obesity comes from the associated diseases and not from the weight gain itself, the confirmation of ACP1 as a modifier gene of metabolic complications of obesity opens the door to possible modulation of this gene product in the treatment of obesity as a safeguard against hyperlipidemia and metabolic syndrome. Today there is intense research going on in the role of tyrosine phosphatases in the pathogenesis of metabolic diseases and/or their clinical variability (24). Until now LMPTP is the only identified PTPase whose polymorphism has been demonstrated to be associated with the clinical variability of obesity in different populations.

Predisposition to hyperlipidemia, especially hyperlipidemia associated with metabolic syndrome, can be ascertained by testing any tissue of a human for the presence of a non-*A allele at the ACP1 locus. For example, a person who has inherited a germline non-*A ACP1 allele would be prone to develop hyperlipidemia, and perhaps metabolic syndrome, if they became obese. The presence of a non-*A ACP1 allele can be determined by testing DNA from any tissue of the person's body. Most simply, blood can be drawn and DNA extracted from the cells of the blood. In addition, prenatal diagnosis can be accomplished by testing fetal cells, placental cells or amniotic cells for a non-*A ACP1 allele. The presence of an *A or a non-*A allele at the ACP1 locus can be detected by any of the means discussed herein.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful are techniques employing DNA microchip technology. (37)

There are several methods well known to persons of ordinary skill in the art that can be used to detect DNA sequence variation, including direct DNA sequencing, clamped denaturing gel electrophoresis, heteroduplex analysis and chemical mismatch cleavage. None of these methods will detect large deletions, duplications or insertions, nor will they detect a regulatory mutation which affects transcription or translation of the protein. Other methods which might detect these classes of mutations, such as a protein truncation assay or the asymmetric assay, detect only specific types of mutations and would not detect missense mutations. Once a mutation is known, an allele-specific detection approach such as allele-specific oligonucleotide (ASO) hybridization can be utilized to rapidly screen large numbers of other samples for that same mutation.

Detection of point mutations can be accomplished by molecular cloning of the allele(s) and sequencing the allele(s) using techniques well known to persons of ordinary skill in the art. Alternatively, the gene sequences can be amplified directly from a genomic DNA preparation using known techniques. The DNA sequence of the amplified sequences then can be determined.

DNA sequences of the gene which have been amplified by use of PCR may also be screened using allele-specific oligomer probes, each of which contains a region of the gene sequence harboring a known mutation. For example, one oligomer may be about 30 nucleotides in length (although shorter and longer oligomers can be used, as recognized by those of ordinary skill in the art), corresponding to a portion of the gene sequence. By use of a battery of such allele-specific probes, PCR amplification products can be screened to identify the presence in an individual of a previously identified gene mutation. Hybridization of allele-specific probes with nucleic acids amplified from cells can be performed, for example, on a nylon filter. Hybridization to a particular probe under high stringency hybridization conditions indicates the presence of the same mutation in the cells as in the allele-specific probe.

Nucleic acid analysis via microchip technology is also applicable to the present invention. In this technique, literally thousands of distinct oligonucleotide probes can be applied in an array on a silicon chip. A nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, or measure expression levels of a gene of interest. The method is one of parallel processing of many, even thousands, of probes at once and can tremendously increase the rate of analysis.

An ACP1 *A allele, or a non-*A allele, can be detected by detection of the corresponding mRNA transcript by any technique known to persons of ordinary skill in the art. These include Northern blot analysis, PCR amplification and RNase protection.

An ACP1 *A allele, or a non-*A allele, also can be detected by screening for the encoded protein. For example, monoclonal antibodies immunoreactive with the protein encoded by the ACP1 *A allele can be used to screen a tissue. Lack of cognate antigen would indicate the presense of a non-*A allele. Antibodies specific for products of non-*A alleles also could be used to detect a non-*A gene product. Such immunological assays can be done in any convenient format known in the art. These include Western blots, immunohistochemical assays and ELISA assays. Functional assays, such as protein binding determinations, also can be used. In addition, assays which detect biochemical function can be used.

The nucleic acid probes provided by the present invention are useful for a number of purposes. They can be used in Southern hybridization to genomic DNA and in the RNase protection method for detecting point mutations. The probes can be used to detect PCR amplification products. They may also be used to detect mismatches with a particular ACP1 allele or mRNA using other techniques.

In order to detect an ACP1 gene allele, a biological sample is prepared and analyzed for a difference between the sequence of the allele being analyzed and the sequence of a reference allele. Alternatively, the presence or absence of a particular allele can be determined by an immunological assay using antibodies specific for the protein produced by a reference ACP1 allele (e.g., the *A allele, the A allele, the B allele, etc.).

Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA) and nucleic acid sequence based amplification (NASBA). These methods are well known and widely practiced in the art. Reagents and hardware for conducting PCR are commercially available. Primers useful to amplify sequences from the region are preferably complementary to, and hybridize specifically to, sequences in the region or in regions that flank a target region therein.

"Antibodies." The present invention also provides polyclonal and/or monoclonal antibodies and fragments thereof, and immunologic binding equivalents thereof, which are capable of specifically binding to the polypeptides and fragments thereof of an ACP1 enzyme encoded by a particular ACP1 allele, or to polynucleotide sequences from the region, particularly from the ACP1 locus or a portion thereof. The term "antibody" is used both to refer to a homogeneous molecular entity, or a mixture such as a serum product made up of a plurality of different molecular entities. Antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known by persons of ordinary skill in the art.

An immunological response is usually assayed with an immunoassay. Normally, such immunoassays involve some purification of a source of antigen, for example, that produced by the same cells and in the same fashion as the antigen. A variety of immunoassay methods are well known by persons of ordinary skill in the art.

Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like.

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

The polynucleotide compositions useful in this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. The polynucleotides useful in the invention may be isolated or substantially pure.

The present invention provides for the use of recombinant nucleic acids comprising the ACP1 *A allele. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are useful in this invention. Although the described sequences may be employed, it will often be altered, e.g., by deletion, substitution or insertion.

cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The recombinant nucleic acid sequences used to produce fusion proteins of the present invention may be derived from natural or synthetic sequences. Many natural gene sequences are obtainable from various cDNA or from genomic libraries using appropriate probes.

"Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with alleles which predispose to metabolic syndrome are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known by persons of ordinary skill in the art.

Probes for alleles may be derived from the sequences of the region or its cDNAs. The probes may be of any suitable length, which span all or a portion of the region, and which allow specific hybridization to the region. If the target sequence contains a sequence identical to that of the probe, the probes may be short, e.g., in the range of about 8-30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences having sequence similarity, by standard methods. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change ligand-binding affinities, interchain affinities, or the polypeptide degradation or turnover rate.

"Protein modifications or fragments" are provided by the present invention for ACP1 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by persons of ordinary skill in the art. A variety of methods for labeling polypeptides and of substituents or labels useful for such purposes are well known by persons of ordinary skill in the art, and include radioactive isotopes such as P, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation.

Besides substantially full-length polypeptides, the present invention provides for the use of biologically active fragments of the polypeptides. Significant biological activities include ligand-binding, immunological activity and other biological activities characteristic of polypeptides.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The present invention also provides for the use of fusion polypeptides, comprising polypeptides and fragments. Homologous polypeptides may be fusions between two or more polypeptide sequences or between the sequences of ACP1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding and may include for example partners such as immunoglobulins, bacterial b-galactosidase, trpE, protein A, b-lactamase, alpha amylase, alcohol dehydrogenase and yeast alpha mating factor.

Fusion proteins will typically be made by either recombinant nucleic acid methods, as described below, or may be chemically synthesized. Techniques for the synthesis of polypeptides are well known by persons of ordinary skill in the art.

Other protein modifications include amino acid substitution. Substitutional variants typically contain the exchange of one amino acid for another at one or more sites within the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known to persons of ordinary skill in the art and typically include, though not exclusively, substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with an polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is further discussed in U.S. Pat. No. 5,691,198.

"Protein purification" refers to various methods for the isolation of polypeptides from other biological material, such as from cells transformed with recombinant nucleic acids encoding ACP1, and are well known by persons of ordinary skill in the art. For example, such polypeptides may be purified by immunoaffinity chromatography employing, e.g., the antibodies provided by the present invention. Various methods of protein purification are well known by persons of ordinary skill in the art.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known by persons of ordinary skill in the art, such as polyacrylamide gel electrophoresis of a protein sample, followed by visualizing a single polypeptide band upon staining the gel. For certain purposes, higher resolution may be provided by using HPLC or other means well known by persons of ordinary skill in the art which are utilized for purification.

A protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known by persons of ordinary skill in the art.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

Large amounts of the polynucleotides of the present invention may be produced by a suitable host cell transformed with a nucleotide sequence encoding the ACP1 protein. Natural or synthetic polynucleotide fragments coding for the peptide or a desired fragment can be incorporated into recombinant polynucleotide constructs (vectors), usually DNA constructs, capable of introduction into and replication in a prokaryotic or eukaryotic cell. Usually the vectors will be suitable for replication in a unicellular host, such as yeast or bacteria, but may also be intended for introduction to (with and without integration within the genome) cultured mammalian or plant or other eukaryotic cell lines. The most commonly used prokaryotic hosts are strains of Escherichia coli, although other prokaryotes, such as Bacillus subtilis or Pseudomonas may also be used. Mammalian or other eukaryotic host cells, such as those of yeast, filamentous fungi, plant, insect, or amphibian or avian species, may also be useful for production of the proteins of the present invention.

Vectors will include an appropriate promoter and other necessary vector sequences that are functional in the selected host. There may include, when appropriate, those naturally associated with genes. Many useful vectors are known in the art and may be obtained from such vendors as Stratagene, New England BioLabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others.

Expression and cloning vectors preferably contain a selectable marker gene. Typical marker genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for Bacilli. The choice of an appropriate proper selectable marker will depend on the host cell, and appropriate markers for different hosts are well known to persons of ordinary skill in the art.

The vectors containing the nucleic acids of interest can be transcribed in vitro, and the resulting RNA introduced into the host cell by well-known methods, e.g., by injection, or the vectors can be introduced directly into host cells by methods well known to persons of ordinary skill in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alia, those described above, will be referred to herein as "transformation." The cells into which have been introduced nucleic acids described above are meant to also include the progeny of such cells.

Clones are selected by using markers, depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention are useful not only for the production of the nucleic acids and polypeptides of the present invention, but also, for example, in studying the characteristics of ACP1 polypeptides.

Antisense polynucleotide sequences are useful in preventing or diminishing the expression of the locus, as will be appreciated by those skilled in the art. For example, polynucleotide vectors containing all or a portion of the locus or other sequences from the region (particularly those flanking the locus) may be placed under the control of a promoter in an antisense orientation and introduced into a cell. Expression of such an antisense construct within a cell will interfere with transcription and/or translation and/or replication.

In order to detect the presence of a non-*A ACP1 allele predisposing an individual to hyperlipidemia, especially hyperlipidemia associated with metabolic syndrome, a biological sample such as blood is prepared and analyzed for the presence or absence of predisposing alleles of ACP1. Such diagnoses may be performed by diagnostic laboratories, or, alternatively, diagnostic kits are manufactured and sold to health care providers or to private individuals for self-diagnosis.

Initially, the screening method can involve amplification of the relevant ACP1 sequences. In another preferred embodiment of the invention, the screening method involves a non-PCR based strategy. Such screening methods include two-step label amplification methodologies that are well known to persons of ordinary skill in the art. Both PCR and non-PCR based screening strategies can detect target sequences with a high level of sensitivity.

Preferred embodiments relating to methods for detecting a non-*A ACP1 allele or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies.

This invention is particularly useful for screening compounds by using a non-*A ACP1 polypeptide or binding fragment thereof in any of a variety of drug screening techniques. There are a number of protein tyrosine phosphatase (PTP) inhibitors known in the art (see e.g., ref. 38). As this reference states, significant progress in developing PTP inhibitors is being made (Burke and Zhang, 1998, Kennedy and Ramachandran, 2000). For example, vanadate and its derivatives such as peroxovanadium complexes are one of the best characterized PTP inhibitors. PTP substrate analogues, in which the cleavable O-P linkage has been replaced by PTP-resistant chemical linkage, such as sulfotyrosine, thiophosphotyrosine, O,O-dicar boxymethyltyrosine, phosphonomethyl phenylalanine, and 4-[difluoro(phosphono)methyl]phenylalanine, have been shown as potent inhibitors of PTPs (Burke et al., 1994, Liotta et al., 1994, Zhang et al., 1994, Kole et al., 1995, Burke et al., 1996, Huyer et al., 1998, Desmarais et al., 1999). Phosphonate compounds incorporated in peptides are being developed as relatively selective inhibitors of PTPs (Chen et al., 1995, Taing et al., 1999). Recently, simple organic molecules such as 2-(ox-alylamino) benzoic acid (OBA) and its derivatives (Andersen et al., 2000, Iversen et al., 2000), and benzofuran and benzothiophen biphenyls compounds (Malamas et al., 2000) have turned out to be potent inhibitors. Keggin compounds phosphomolybdate (PM) and phosphotungstate (PT) strongly inhibit PTPs. Phosphate analogs such as vanadate, molybdate, and tungstate inhibit both PTP-1B and SHP-1, with $K_i$ values in micromolar ranges under the assay conditions used. Thiophosphate appears to selectively inhibit SHP-1, and derivatives of vanadate such as peroxovanadyl compounds (Posner et al., 1994) and vanadylsulfate also appears to effectively inhibit both PTP-1B and SHP-1. Phosphomolybdate (PM) and phosphotungstate (PT) work as potent, competitive, and reversible inhibitors against PTP-1B and SHP-1. PM and PT appear to strongly inhibit other PTPs such as LAR, but they weakly inhibit Ser/Thr phosphatase, but do not inhibit alkaline phosphatase at all. Unexpectedly, the crystal structure of PTP-1B complexed with PM reveals that $MoO_3$, derived from PM by hydrolysis, binds at the active site. The molybdenum atom of the inhibitor is six-coordinated with three oxo-ligands from $MoO_3$, two apical water molecules and a S atom from the catalytic cysteine residue. PM and PT reversibly inhibit PTPs, with $K_i$ values in the nanomolar range, in the presence of 1 mM EDTA. These $K_1$ values are about 50 times lower than the $K_i$ value of vanadate. Most of the potent PTP inhibitors so far reported display $K_i$ values in the hundred-nanomolar range. For example, the $K_i$ value of vanadate against PTP-1B has been reported to be 0.38 µM in the absence of EDTA (Huyer et al., 1997). The lowest $K_i$ value of the $F_2Pmp$ containing peptide, against rat PTP1, has been reported to be 0.12 µM at pH 7.0 (Chen et al., 1995). Iverson et al. (2000) reported the $K_i$ value of an OBA derivatives, against PTP-1B, as 0.29 µM at pH 5.1. PM and PT seem to be one of the most potent PTP inhibitors so far developed judging from the reported $K_i$ values. PM and PT potently inhibit cytoplasmic PTPs such as PTP-1B and SHP-1, and receptor-like PTPs such as LAR. The catalytic PTP domains contain a distinct sequence motif of 11 amino acid residues, I/VHCXXGXXRS/TG, at the active site. The Cys residue is critical in the catalytic activity of PTPs functioning as a nucleophile that form a thiol-phosphate intermediate during catalysis (Guan and Dison, 1991, Zhou et al., 1994). The Cys residue is easily inactivated by sulfhydryl oxidizing and alkylating agents (Zhang and Dixon, 1993). The crystal structure of PTP-1B, complexed with PM, reveals that $MoO_3$ binds at the active site forming a thiol-molybdenum ester linkage between the Cys residue and the central molybdenum atom. Polyanionic Keggin compounds, PM $(12MoO_3.H_3PO_4)$ and PT $(12WO_3.H_3PO_4)$ contain twelve $MoO_3$ or $WO_3$ moieties, and one $PO_4$ moiety in the molecular structure. Those Keggin compounds are known to hydrolyze in aqueous solution to an equilibrium concentration of various compounds. Molybdenum oxides $(Mo_3$, $MoO_3$ and $MoO_2Cl_2)$ inhibited PTPs, however, the inhibition potential of $MoO_3$ appeared to be lower than PM, considering PM contains 12 $MoO_3$ units. Vanadate is a phosphate analog, since it can adopt a similar structure to inorganic phosphate. The three dimensional structure of the PTP-1B complexed with vanadate reveals that the vanadate molecule occupies the active site forming a thiol-vanadyl ester linkage between the central vanadium atom and the S atom of Cys215, which is colinar with the apical oxygen-vanadium bond (Pannifer et al., 1998). Thus the vanadate in the active site forms a pentavalent trigonal bipyramidal structure. The structure of vanadate, complexed with PTP-1B, is very similar to the transition state of the cysteinyl-phosphate intermediate when being attacked by a nucleophilic water, forming a pentavalent phosphorus intermediate (Denu et al., 1996). The apical oxygen of the vanadate is hydrogen bonded with amide side chains of Gln262. The side chain of Asp181 also interacts with the apical oxygen, causing the closed conformation of the WPD loop (residues 179-187). Tungstate has also been shown to bind at the active site of PTP (Barford et al., 1994), forming a distorted trigonal bipyramidal structure. However, in the tungstate-complexed PTP-1B, the side chain of Gln262 does not bind tightly to the tungstate. The shortest length, between the apical oxygen of tungstate and the amide side chain of Gln262, is just 3.8 A. Similar to the case of vanadate or tungstate, $MoO_3$ binds to the active site of the PTP-1B. However, the binding mode and conformation of $MoO_3$, complexed with PTP-1B, appear to be quite distinct. Most importantly, $MoO_3$ bound to the active site exhibits an extremely distorted hexavalent octahedral geometry, with three oxoligands, and three additional ligands from a sulfur atom of Cys215 and from two oxygen atoms of water molecules. It has been observed from the structure of PTP-1B complexed with a FOMT-based cyclic peptide, which has a $K_1$ value of 0.17 mM, the closure of the WPD loop is not essential for the high inhibitory potential of PTP inhibitor. For example, vanadylsulfate and vanadyl[bis(maltalato)oxovanadium (IV)] have been synthesized, and shown to inhibit PTPs with similar potency to vanadate (Yuen et al., 1993). A variety of vanadate complexes including bismaltooxovanadates, and peroxovanadates with different ancillary ligands, have been synthesized. Some of these have been shown to increase the level of insulin receptor phosphorylation (Posner et al., 1994, Poucheret et al., 1998). Recently, a complex of vanadate with dimethyldroxylamine ha been synthesized and shown to reversibly inhibit PTP-1B and LAR, with a $K_1$ in the micromolar range. Heo et al., Exp. Mol. Med. 34(3):211-223.

It is a matter of routine experimentation in the pharmaceutical arts to screen such compounds for activity specifically against ACP1, and subsequently to evaluate potential drugs for toxicity, side-effects, etc. to determine their ultimate suitability for in vivo use in humans. For example, the polypeptide or fragment employed in such a test may either be free in solution, affixed to a solid support, or borne on a cell surface. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a non-*A ACP1 polypeptide or fragment and the agent being tested, or examine the degree to which the formation of a complex between a non-*ACP1 polypeptide of the invention or fragment and a known ligand. Alternatively, one may measure the enzymatic activity of the ACP1 protein in the presence of the agent being tested, either by measuring the rate of formation of a reaction product (e.g., dephosphorylated ALBP, or free phosphate) or the disappearance of a substrate, such as ALBP.

Following identification of a substance which modulates or affects activity of the non-*A ACP1 enzyme, the substance may be investigated further. Furthermore, it may be manufactured and/or used in preparation, i.e., manufacture or formulation, or a composition such as a medicament, pharmaceutical composition or drug. These may be administered to individuals. Thus, the present invention extends, in various aspects, not only to a substance identified using a nucleic acid molecule as a modulator of polypeptide activity, in accordance with what is disclosed herein, but also to a pharmaceutical composition, medicament, drug or other composition comprising such a substance, methods comprising administration of such a composition comprising such a substance, methods comprising administration of such a composition to a patient, e.g., for treatment of metabolic syndrome, use of such a substance in the manufacture of a composition for administration, e.g., for treatment of hyperlipidemia and/or metabolic syndrome, and a method of making a pharmaceutical composition comprising admixing such a substance with a pharmaceutically acceptable excipient, vehicle or carrier, and optionally other ingredients.

The present invention contemplates an antisense polynucleotide that hybridizes with mRNA molecules that encode a non-*A ACP1 polypeptide, and the use of one or more of those polynucleotides in treating metabolic syndrome. An antisense polynucleotide can for example be administered by gene therapy. The polynucleotide may be introduced into the cell in a vector such that the polynucleotide remains extrachromosomal. In such a situation, the polynucleotide will be expressed by the cell from the extrachromosomal location. Vectors for introduction of polynucleotides for extrachromosomal maintenance are known in the art, and any suitable vector may be used. The antisense polynucleotide may be employed in gene therapy methods in order to decrease the amount of the expression products of a non-*A ACP1 in persons predisposed to, or suffering from, hyperlipidemia, especially hyperlipidemia associated with metabolic syndrome.

Cells and animals which carry a specific ACP1 allele can be used as model systems to study and test for substances which have potential as therapeutic agents. The cells are typically cultured cells and may be isolated from individuals having the allele of interest. Alternatively, the cell line or animal can be engineered to carry the ACP1 allele of interest using standard techniques well-known in the art. After test substances have been administered to the animals, the animals are assessed for hyperlipidemia, and/or expression of other symptoms associated with metabolic disorder, including obesity, hypertension, non-insulin dependent diabetes and coronary artery disease. These animal models provide an extremely important testing vehicle for potential therapeutic products. Alternatively, as described above, ACP1 activity can be measured in the cells or animal. Reduction in ACP1 activity relative to controls indicates suitability as a therapeutic agent for treating or preventing hyperlipidemia, especially hyperlipidemia associated with metabolic syndrome. Further analysis of potential drugs thus identified, to assess specificity, toxicity, side effects, etc., is a matter of routine experimentation in the pharmaceutical arts.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982 (28); Sambrook et al., 1989 (32); Ausubel et al., 1992 (26); Anand, 1992 (25); *Culture Of Animal Cells* (R. I. Freshney, Alan R. Liss, Inc., 1987) (27); *Immobilized Cells And Enzymes* (IRL Press, 1986) (34); B. Perbal, *A Practical Guide To Molecular Cloning* (1984) (30); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory) (29); *Methods In Enzymology*, Vols. 154 and 155 (Wu et al. eds.) (33), *Immunochemical Methods In Cell And Molecular Biology* (Mayer and Walker, eds., Academic Press, London, 1987) (35); Riott, *Essential Immunology*, 6th Edition, Blackwell Scientific Publications, Oxford, 1988 (31); Hogan et al., *Manipulating the Mouse Embryo*, (Cold Spring Harbor Laboratory Press, Cold Spring Harbor, N.Y., 1986) (36).

The present invention is described by reference to the following Examples, which are offered by way of illustration and are not intended to limit the invention in any manner. Standard techniques well known by persons of ordinary skill in the art and/or the techniques specifically described below were utilized.

EXAMPLE 1

A study was performed at the Center for Health Promotion at Loma Linda University Medical Center, Loma Linda, Calif. Non-Hispanic Caucasian females (average age 54.5.+−.6.5 [SD] years) with a lifetime history of obesity (average BMI 39.1.+−.7.5 [SD]) were recruited from the community by newspaper ads. To obtain a broad range of BMI, each currently obese subject was asked to bring to the clinic an age matched non-obese friend from her own ethnic, educational and social class. Using the criteria described by Trakas et al (13) subjects were classified into three weight groups: BMI≦29=non-obese; BMI 30-34=obese; BMI≧35=morbidly obese. The obese and morbidly obese subjects had an average BMI of 39.1±7.5 [SD]. The non-obese subjects had an average BMI of 24.0±2.7 [SD]. All subjects were unrelated, were drug-free, and were specifically not taking lipid lowering agents or blood pressure medication. Blood lipid levels were performed on individuals fasted overnight. The cholesterol, triglycerides and HDL were determined by enzymatic assay (DuPont Dimension analyzer), and the LDL was calculated from these results.

The ACP1 polymorphism was determined with an RFLP-PCR method as follows: an A to G transversion at the nt 24 of the exon 6 (GenBank GI:178004) creates in the *A allele a restriction site for TaqI (14), while a C to T transition at the nt 15 of the exon 3 (GenBank GI:306443) removes in the *C allele a restriction site for HhaI (Sensabaugh G, unpublished). Both the TaqI and HhaI restriction polymorphisms have been determined by RFLP-PCR after amplification respectively of fragments of the exon 6 and exon 3 and digestion of the PCR product with an excess of the relative restriction enzyme. In both determinations the forward primers contained a fixed restriction site for HhaI and for TaqI, which was used as an internal control. One hundred fifty-one obese subjects were genotyped for both the TaqI and HhaI polymorphisms, 26 additional obese subjects and all non-obese subjects were genotyped for the non-*A (TaqI) polymorphism only. Chi square test, ANOVA, Students T-test, Levene's test for homogeneity of variance, MANOVA and correlation analyses were performed using the SPSS program (15).

ACP1 genotype frequencies showed no significant deviation from Hardy-Weinberg expectation in the samples, and no significant association was found between ACP1 polymorphism and BMI. Table I shows the number of subjects in each of the BMI groups by number of subjects in each genotypes. Homozygocity for the A allele is fairly rare. Since this was an uncommon genotype and since there was no consistent tendency for the A/A nucleotide genotype to show a lower triglyceride level than the T/A genotype, in all analyses the T/A and A/A genotypes were combined into a group termed *A carrier. An ANOVA analysis was performed in the subgroup of obese subjects genotyped for both the *A/not*A and the *C/not*C SNPs, with the ACP1 polymorphism as independent variable and clinical variables (BMI, total cholesterol, HDL cholesterol, LDL cholesterol, Cholesterol/HDL ratio, triglycerides and fasting glucose) as dependent variables. The analysis showed that a highly significant association of ACP1 polymorphism with cholesterol and with triglycerides levels present in the obese sample was due to an effect of the *A rather than the *C allele (data not shown).

TABLE I

ACP1 Genotype in the 277 non-Hispanic Caucasian females studied

|  | Non A/Non A | Non A/A | A/A | Total |
|---|---|---|---|---|
| BMI 29 or less | 39 (48%) | 35 (43%) | 8 (10%) | 82 |
| BMI 30-34 | 31 (52%) | 27 (45%) | 2 (3%) | 60 |
| BMI 35 or more | 62 (46%) | 56 (42%) | 17 (13%) | 135 | p = n.s.

Table II shows the results of ANOVA of the association of the *A carrier (*A/*A, *A/*B and *A/*C) genotypes versus the non-*A carrier (*B/*B, *B/*C and *C/*C) genotypes for different biochemical variables in the obese subjects (BMI≧30). There was a significant increase in the total cholesterol, LDL cholesterol, cholesterol/HDL ratio, and triglyceride levels in non-*A carriers versus *A allele carriers. There was borderline association with waist-hip ratio. There was no association of the *A allele with BMI or blood lipids in the non-obese subjects. A MANOVA test using age as a co-variate showed these results were independent of age.

TABLE II

Associations between *A allele and BMI, BLL and fasting glucose level in 195 obese post-menopausal women

|  | *A carrier (N = 102) | non-*A carrier (N = 93) | p |
|---|---|---|---|
| BMI | 38.7 (8.2) | 38.0 (6.0) | n.s. |
| Total Cholesterol (mg/dl) | 207.4 (39.6) | 224.1 (39.1) | 0.002 |
| HDL Cholesterol (mg/dl) | 54.7 (12.8) | 53.1 (13.4) | n.s. |
| LDL Cholesterol (mg/dl) | 117.9 (35.5) | 132.7 (37.3) | 0.015 |
| Cholesterol/HDL ratio | 3.9 (1.1) | 4.4 (1.3) | 0.006 |
| Triglyceride (mg/dl) | 165.2 (74.4) | 207.3 (105.1) | 0.001 |
| Fasting Glucose (mg/dl) | 105.2 (29.0) | 113.8 (50.1) | n.s. |
| Waist-Hip Ratio | .823 (.13) | .857 (.123) | 0.09 |

Grouping the ACP1 genotypes according to their known enzymatic activity (8), as shown in Table 1, a Pearson correlation analysis of putative enzymatic parameters (total activity, A and B isoform concentration and A/B ratio), associated with ACP1 genotypes, and BMI, total cholesterol and triglyceride showed a significant positive correlation of both the amount of total enzymatic activity and of A isoform activity associated with ACP1 genotypes and total cholesterol (R=0.204, p=0.01 for total activity) and triglyceride (R=0.227, p=0.005 for total activity). No association was present with B isoform and A/B activity ratio (data not shown).

FIG. 1 shows the relationship between ACP1 polymorphism and triglyceride levels for subjects grouped according to their classification as non-obese, obese or morbidly obese (13). The relationship of ACP1 genotype with triglyceride concentrations is positively associated with BMI in obese subjects and this finding was more pronounced in morbidly obese subjects. An ANOVA analysis performed in *A allele carriers and non-*A allele carriers separately showed that the increase of BMI is significantly associated with the development of hypertriglyceridemia in non-*A allele carriers only (p=0.001 for non-*A carriers, p=0.076 for *A carriers). These data indicates that the ACP1 *A allele exerts a strong protective effect against the development of hypertriglyceridemia in obese subjects. A similar relationship was found between ACP1 and cholesterol levels in different classes of BMI, but it didn't reach statistical significance (data not shown).

REFERENCES

1. Abate N. Obesity and cardiovascular disease. 2000 Pathogenetic role of the metabolic syndrome and therapeutic implications. J Diabetes Complications. 14: 154-74.
2. Allison D B, Fontaine K R, Manson J E, Stevens J, Vanitallie T B. 1999 Annual, deaths attributable to obesity in the United States. AMA. 282:1530-8.
3. Alexander J K. 2001 Obesity and coronary artery disease. Am J Med. Sci. 321: 215-24.
4. Duriez P, Fruchart J C. 1999. Recent developments in the treatment of hypertriglyceridemia. Curr Atheroscler Rep. 1:31-7.
5. Ramponi G, Stefani M. 1997 Structure and function of the low Mr phosphotyrosine protein phosphatases. Biochim Biophys Acta. 1341:137-56.
6. Cirri P, Fiaschi T, Chiarugi P, Camici G, Manao G, Raugei G, Ramponi G. 1996 The molecular basis of the differing kinetic behavior of the two low molecular mass phosphotyrosine protein phosphatase isoforms. J Biol. Chem. 271: 2604-7.
7. Shekels L L, Smith A J, Van Etten R L, Bemlohr D A. 1992 Identification of the adipocyte acid phosphatase as a PAO-sensitive tyrosyl phosphatase. Protein Sci. 1:710-21.
8. Dissing J. 1993 Human "red cell" acid phosphatase (ACP1) genetic, catalytic and molecular properties. PhD Thesis. Kobenhavn Universitat, Kobenhavn, Denmark.
9. Lucarini N, Finocchi G, Gloria-Bottini F, Macioce M, Borgiani P, Amante A, Bottini E. 1990 A possible genetic component of obesity in childhood. Observations on acid phosphatase polymorphism. Experientia. 46:90-1.
10. Bottini E, Lucarini N, Gerlini G, Finocchi G, Scire G, Gloria-Bottini F. 1990 Enzyme polymorphism and clinical variability of diseases: study of acid phosphatase locus 1 (ACP1) in obese subjects. Hum Biol. 62:403.
11. Paggi A, Borgiani P, Gloria-Bottini F, Russo S, Saponara I, Banci M, Amante A et al. 1991 Further studies on acid phosphatase in obese subjects. Dis Markers. 9:1-7.

12. Lucarini N, Antonacci E, Bottini N, Gloria Bottini F. 1997 Low-molecular-weight acid phosphatase (ACP1), obesity, and blood lipid levels in subjects with non-insulin-dependent diabetes mellitus; Hum Biol. 69:509-15.
13. Trakas K, Oh P I, Singh S, Risebrough N, Shear N H. 2001 The health status of obese individuals in Canada. Int J Obes Relat Metab Disord. 25:662-8.
14. Sensabaugh O F and Lazaruk K A. 1993 A Taql site identifies the *A allele at the ACP1 locus. Hum Mol. Genet. 2:1079.
15. SPSS/PC+ Version 5.0. 1992 SPSS Inc, Chicago, Ill.
16. Dissing J, Johnsen A H. 1992 Human red cell acid phosphatase (ACP1): the primary structure of the two pairs of isozymes encoded by the ACP1 *A and ACP1 *C alleles. Biochim Biophys Acta. 1121:261-8.
17. Chiarugi P, Cirri P, Marra F, Raugei G, Camici G, Manao G, Ramponi G. 1997 LMW-PTP is a negative regulator of insulin-mediated mitotic and metabolic signalling. Biochem Biophys Res Commun. 238:676-82.
18. Buelt M K, Xu Z, Banaszak L J, Bernlohr D A. 1992 Structural and functional characterization of the phosphorylated adipocyte lipid-binding protein (pp 15). Biochemistry. 31:3493-9.
19. Chagnon Y C, Perusse L, Weisnagel S J, Rankinen T, Bouchal D C. 2000 The human obesity gene map: the 1999 update. Obes Res. 8:89-117.
20. Elchebly M, Cheng A, Tremblay M L. 2000 Modulation of insulin signaling by protein tyrosine phosphatases. J Mol. Med. 78:473-82.
21. Liao K, Hoffman R D, Lane M D. 1991 Phosphotyrosyl turnover in insulin signaling. Characterization of two membrane-bound pp15 protein tyrosine phosphatases from 3T3-L1 adipocytes. J Biol. Chem. 266:6544-53. I
22. Caselli A, Taddei M L, Manao G, Camici G, Ramponi G. 2001 Tyrosine-phosphorylated caveolin is a physiological substrate of the low Mr protein-tyrosine phosphatase. J Biol. Chem. 276:18849-54.
23. Okamoto T, Schlegel A, Scherer P E, Lisanti M P. 1998 Caveolins, a family of scaffolding proteins for organizing "preassembled signaling complexes" at the plasma membrane. J. Biol. Chem. 273:5419-22.
24. Zhang B B, Moller D E. 2000 New approaches in the treatment of type 2 diabetes. Curr Opin Chem. Biol. 4:461-7.
25. Anand, R. Techniques for the Analysis of Complex Genomes, (Academic Press) 1992.
26. Ausubel, F. M., et al. Current Protocols in Molecular Biology, (J. Wiley and Sons, NY) 1992.
27. Freshney, Alan R. Liss, Inc. Culture Of Animal Cells 1987.
28. Maniatis. T., et al Molecular Cloning: A Laboratory Manual (Cold Spring Harbor Laboratory, Cold Spring Harbor, N.Y.) 1982.
29. Miller, J. H. and M. P. Calos eds.: Gene Transfer Vectors For Mammalian Cells, 1987, Cold Spring Harbor Laboratory).
30. Perbal, A Practical Guide To Molecular Cloning 1984. Methods In Enzymology (Academic Press, Inc., N.Y.)
31. Roitt, Essential Immunology, 6th Edition, Blackwell Scientific Publications, Oxford, 1988.
32. Sambrook, J., et al. Molecular Cloning: A Laboratory Manual, 2nd Ed. (Cold Spring Harbor Laboratory, Cold Spring Harbor, N.Y.) 1989.
33. Wu et al. eds.: Methods In Enzymology, Vols. 154 and 155.
34. Immobilized Cells And Enzymes (IRL Press, 1986).
35. Immunochemical Methods In Cell And Molecular Biology (Mayer and Walker, eds., Academic Press, London, 1987) (35).
36. Hogan et al., Manipulating the Mouse Embryo, (Cold Spring Harbor Laboratory Press, Cold Spring Harbor, N.Y.) 1986.
37. McGall, G. H. and F. C. Christians, 2002, High-density gene chopolinucleotide probe arrays, Abd. Biochem. Eng. Biotechnol. 77:21-42.
38. Heo, Y. S., et al., 2002, Structural basis for inhibition of protein tyrosine phosphotases by Keggin compounds phosphomolybdate and phosphotunstate, Exp. Mol. Med. 34:211-213.

What is claimed is:

1. A method of treating or attenuating hyperlipidemia in a subject in need thereof, comprising: introducing into said cell a polynucleotide composition, wherein said polynucleotide composition interferes with a parameter selected from the group consisting of transcription, translation and both transcription and translation, of non-*A ACP-1 alleles, and wherein said polynucleotide does not comprise an ACP-1-*A allele-specific antisense nucleotide molecule.

2. The method of claim 1, wherein said polynucleotide composition comprises polydeoxyribonucleic acid.

3. The method of claim 1, wherein said polynucleotide composition comprises polyribonucleic acid.

4. The method of claim 1, wherein said polynucleotide composition hybridizes with an mRNA molecule that encodes an ACP-1 polypeptide.

* * * * *